US009218687B2

(12) United States Patent
Hill et al.

(10) Patent No.: US 9,218,687 B2
(45) Date of Patent: Dec. 22, 2015

(54) DISPLAY OF MEDICAL DEVICE POSITION INFORMATION IN A VOLUMETRIC RENDERING

(75) Inventors: Anthony D. Hill, Minneapolis, MN (US); Mark Kudas, Astoria, NY (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 813 days.

(21) Appl. No.: 12/982,577

(22) Filed: Dec. 30, 2010

(65) Prior Publication Data

US 2012/0169712 A1 Jul. 5, 2012

(51) Int. Cl.
G06T 15/00 (2011.01)
G06T 15/08 (2011.01)
G06T 19/00 (2011.01)
A61B 5/00 (2006.01)
A61B 5/06 (2006.01)

(52) U.S. Cl.
CPC ............... *G06T 15/08* (2013.01); *A61B 5/062* (2013.01); *A61B 5/7425* (2013.01); *G06T 19/00* (2013.01); *G06T 2219/028* (2013.01)

(58) Field of Classification Search
CPC .... A61B 19/5244; A61B 19/50; A61B 5/062; A61B 5/7425; A61M 2025/0166; G06T 15/08; G06T 19/00; G06T 2219/028
USPC ......... 345/319, 420, 619, 629, 631, 419, 421, 345/424; 600/424, 478; 382/128
See application file for complete search history.

(56) References Cited

U.S. PATENT DOCUMENTS

| 5,734,384 | A | * | 3/1998 | Yanof et al. | ............... 345/424 |
| 5,995,108 | A | * | 11/1999 | Isobe et al. | ............... 345/421 |
| 7,263,397 | B2 | | 8/2007 | Hauck et al. | |
| 7,386,339 | B2 | | 6/2008 | Strommer et al. | |
| 7,840,254 | B2 | * | 11/2010 | Glossop | ............... 600/424 |
| 8,131,350 | B2 | * | 3/2012 | Saadat et al. | ............... 600/478 |
| 8,150,111 | B2 | * | 4/2012 | Borland et al. | ............... 382/128 |
| 8,311,613 | B2 | * | 11/2012 | Danehorn | ............... 600/424 |
| 8,428,690 | B2 | * | 4/2013 | Li et al. | ............... 600/424 |
| 8,494,614 | B2 | * | 7/2013 | Markowitz et al. | ............... 600/424 |
| 2008/0137927 | A1 | | 6/2008 | Altmann et al. | |

(Continued)

OTHER PUBLICATIONS

Fitzpatrick, MmChael J. et al., "Handbook of Medical Imaging: vol. 2. Medical Image Processing", Fitzpatrick et al. Chapter 8: Image Registration Handbook of Medical Imaging: vol. 2.. Medical Image Processing and Analysis, eds. Beutel et al., SPIE Press 2000), Chapter 8: image Registration, pp. 449-514.*

(Continued)

*Primary Examiner* — Phu K Nguyen
(74) *Attorney, Agent, or Firm* — Dykema Gossett PLLC

(57) ABSTRACT

An system and method for displaying a position of a medical device disposed within a region of interest in a body are provided. The system includes a position sensing system disposed outside of the body and configured to interact with a position sensor on the medical device upon generation of an electric and/or magnetic field. The sensor generates a position signal indicative of the position of the device within a coordinate system. The system further includes an electronic control unit comprising a registration module for registering a volumetric data set within the coordinate system. The unit further comprises a generation module for generating a volumetric rendering of the region of interest from the volumetric data set and a superimposition module for superimposing a representation of the medical device on the volumetric rendering responsive to the position signal.

27 Claims, 4 Drawing Sheets

(56) References Cited

U.S. PATENT DOCUMENTS

2009/0163810 A1 6/2009 Kanade et al.
2010/0168557 A1 7/2010 Deno et al.
2010/0168560 A1 7/2010 Hauck et al.

OTHER PUBLICATIONS

Coolignon et al, Automated Multimodality Image Registration using Information Theory, Information Processing in Medical Imaging, 1995, pp. 263-274.*

Biosense Webster, Inc., "AcuNav Ultrasound Catheter," 4 pages (copyright 2006).

Biosense Webster, Inc., "CartoSound Image Integration Module With SoundStar Catheter," 4 pages (copyright 2007).

Singh, Sheldon M. et al., "Image Integration Using Intracardiac Ultrasound to Guide Catheter Ablation of Atrial Fibrillation," 5 Journal of Heart Rhythm No. 11 pp. 1548-1555 (Nov. 2008).

Zhong, Hua, "Image Guided Navigation for Minimally Invasive Surgery," Thesis, Carnegie Mellon Univesrity Computer Science Department (Sep. 24, 2007).

Zhong, Hua, "Image Guided Navigation for Minimally Invasive Surgery," Thesis, Carnegie Mellon University Computer Science Department (Oct. 23, 2007).

* cited by examiner

DISPLAY OF MEDICAL DEVICE POSITION INFORMATION IN A VOLUMETRIC RENDERING

BACKGROUND OF THE INVENTION a. Field of the Invention

This invention relates to a system and method for displaying a position of a medical device disposed within a region of interest in a body. In particular, the invention relates to a system and method that generate a volumetric rendering of the region of interest while simultaneously displaying the position of the medical device within the region of interest.

b. Background Art

It is desirable to track the position of medical devices such as catheters as they are moved within a body so that, for example, drugs and other forms of treatment are administered at the proper location and medical procedures can be completed more efficiently and safely. One conventional means to track the position of medical devices within the body is fluoroscopic imaging. Fluoroscopy is disadvantageous, however, because it subjects the patient and clinician to undesirable levels of high-energy electromagnetic radiation. As a result, medical device navigation systems have been developed to track the position of medical devices within the body. These systems typically rely on the generation of electrical or magnetic fields and the detection of induced voltages and currents on position sensors attached to the medical device. The information derived from these systems is then provided to a clinician through, for example, a visual display.

Conventional systems display the position of a medical device within two dimensional images of the region of interest or within three dimensional models of the region of interest generated from a collection of two-dimensional image slices. Conventional three-dimensional display systems, however, rely on segmentation of the image to identify surface boundaries and create a polygonal mesh. Although such systems have proven useful for their intended purpose, the process of segmentation and boundary identification generates a three-dimensional image that may misidentify structures and removes nuanced local information about the tissue types and thicknesses that are useful in the operation of the medical device relative to the region of interest The inventors herein have recognized a need for a system and method for displaying a position of a medical device disposed within a region of interest in a body that will minimize and/or eliminate one or more of the above-identified deficiencies.

BRIEF SUMMARY OF THE INVENTION

It is desirable to provide a system and method for displaying a position of a medical device disposed within a region of interest in a body. In particular, it is desirable to provide a system and method that generate a volumetric rendering of the region of interest while simultaneously displaying the position of the medical device within the region of interest.

A system for displaying a position of a medical device disposed within a region of interest in a body in accordance with one embodiment of the present teachings includes a position sensing system disposed outside of the body and configured to interact with a position sensor on the medical device upon generation of at least one of an electric field and a magnetic field. The position sensor generates a position signal indicative of the position of the medical device within a coordinate system. The system further includes an electronic control unit comprising a registration module for registering a volumetric data set within the coordinate system. The electronic control unit further comprises a generation module for generating a volumetric rendering from the volumetric data set. The volumetric rendering can include one or more panels displaying a three-dimensional representation (i.e., ray-casted) of the region of interest or single-plane cross-sections through the region of interest according to standard volumetric display techniques. The electronic control unit further comprises a superimposition module for superimposing a representation of the medical device on the volumetric rendering responsive to the position signal.

A method for displaying a position of a medical device disposed within a region of interest in a body in accordance with one embodiment of the present teachings includes the step of generating a position signal indicative of the position of the medical device within coordinate system. The position signal is generated by a position sensor disposed on the medical device and configured to interact with a position sensing system disposed outside of the body upon generation of at least one of an electric field and a magnetic field. The method also includes the step of registering a volumetric data set in the coordinate system. The method further includes the step of generating a volumetric rendering from the volumetric data set. The volumetric rendering can include one or more panels displaying a three-dimensional representation (i.e., ray-casted) of the region of interest or single-plane cross-sections through the region of interest according to standard volumetric display techniques. The method further includes the step of superimposing a representation of the medical device on the volumetric rendering responsive to the position signal.

A system and method in accordance with the present teachings are advantageous as compared to conventional systems and methods because the inventive system and method provide a more accurate and realistic image of the region of interest and of the position of the medical device within the region of interest. As a result, the clinician can more readily navigate medical devices within the region of interest as well as identify structures of interest within the region of interest.

The foregoing and other aspects, features, details, utilities and advantages of the present invention will be apparent from reading the following description and claims, and from reviewing the accompanying drawings.

DETAILED DESCRIPTION OF EMBODIMENTS OF THE INVENTION

Figure 1:
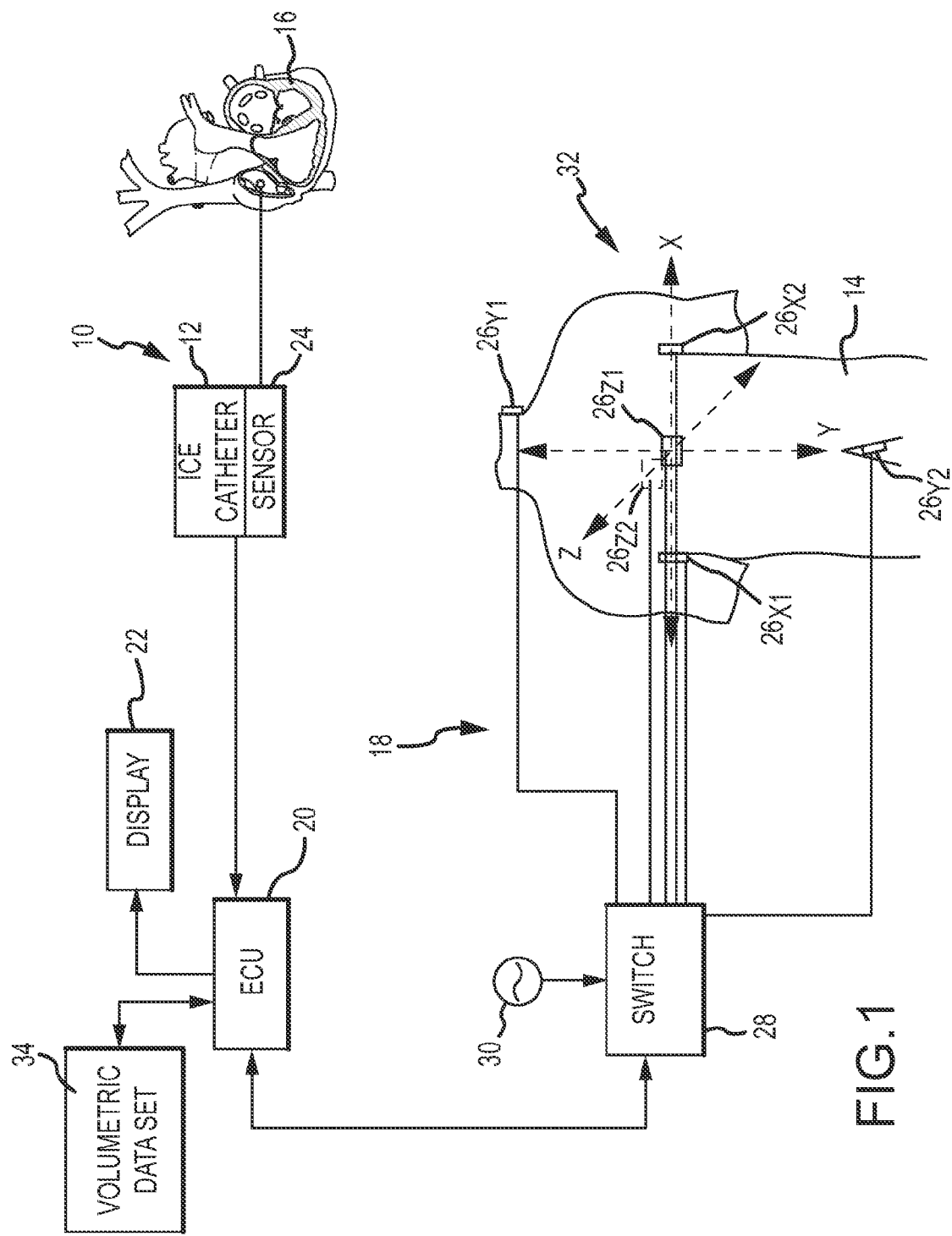
FIG. 1 is a diagrammatic view of a system in accordance with one embodiment of the present teachings.

Referring now to the drawings wherein like reference numerals are used to identify identical components in the various views, FIG. 1 illustrates one embodiment of a system 10 for displaying a position of a medical device 12 disposed within a region of interest in a body 14 such as a heart 16. Although the region of interest is a heart 16 in the illustrated embodiment, it should be understood that the system and method disclosed herein could be applied to other regions of interest within body 14. System 10 may include a position sensing system 18, an electronic control unit (ECU 20) and a display 22.

Figure 4:
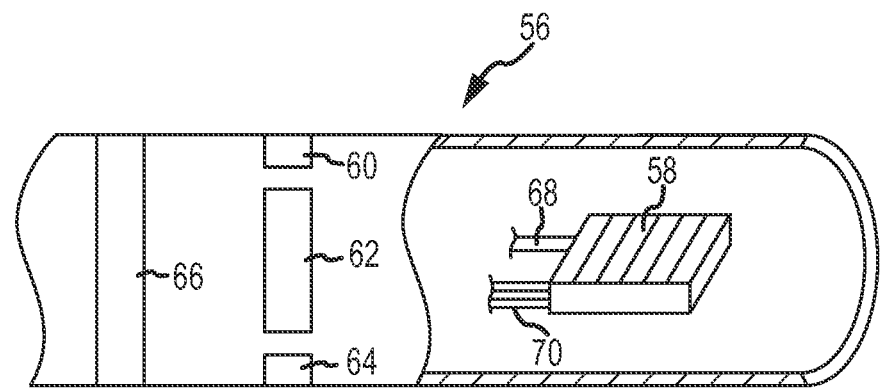
FIGS. 4 and 5 are diagrammatic views of intracardiac echocardiography catheters.
Figure 5:
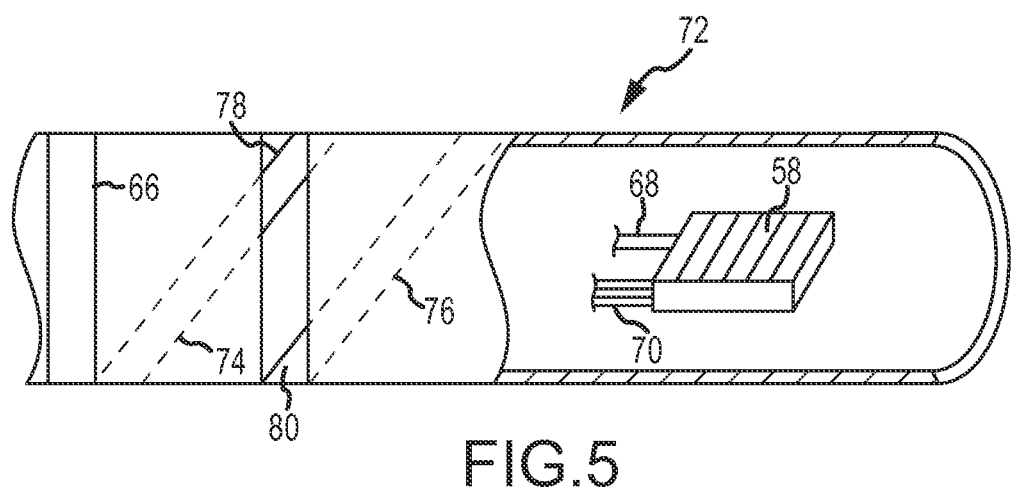

Device 12 is provided for the diagnosis and/or treatment of tissues within body 14 such as cardiac tissue. In the illustrated embodiment, device 12 comprises an intracardiac echocardiography (ICE) catheter. It should be understood, however, that the system and method as described herein could be used with other medical devices including, but not limited to, electrophysiological (EP) mapping catheters and ablation catheters. Device 12 includes one or more position sensors 24 mounted thereon that are configured to generate an induced current or voltage based on the location of sensors within a electric or magnetic field generated by system 18. Sensors 24 may comprise electrodes or coils, for example. Referring to FIG. 4 an exemplary ICE catheter 56 is shown. Catheter 56 include a conventional transducer array 58 and a plurality of electrodes 60, 62, 64, 66 acting as the position sensors 24. The position and orientation of array 58 is controlled in a conventional manner (e.g., through a physician activated or a motor driven shaft 68) and array 58 provides ultrasound data (i.e. two dimensional slice image data) to ECU 20 through conductors 70 connected to array 58. In the embodiment shown in FIG. 4, three electrodes 60, 62, 64 are equally spaced circumferentially about catheter 56 and, together with electrode 66 provide position and orientation data to ECU 20 such that the position and orientation of catheter 56—and the image data provided by array 58—can be determined in six degrees of freedom. Referring to FIG. 5, in an alternate embodiment, a catheter 72 includes ring electrodes 74, 76 that are angled relative to a plane extending perpendicular to an axis extending through the annular center of each electrode 74, 76. As a result, portions 78, 80 of electrodes 74, 76 overlap and are disposed within a common plane. Electrodes 74, 76 may be covered with a thermoplastic elastomer such as the elastomer sold under the trademark "PEBAX" by Arkema of France. Thereafter, the elastomer covering portions 78, 80 may be removed to produce substantially co-planar electrodes that, together with electrode 66, provide position and orientation data to ECU 20 such that the position and orientation of catheter 72—and the image data provided by array 58—can be determined in six degrees of freedom.

System 18 is provided to determine the position and orientation of device 12 and similar devices within body 14 and provides a means for generating a position signal indicative of a position of device 12 within a coordinate system 32. System 18 may comprise the system offered for sale under the trademark "ENSITE NAVX" by St. Jude Medical, Inc. and described in U.S. Pat. No. 7,263,397 titled "Method and Apparatus for Catheter Navigation and Location Mapping in the Heart," the entire disclosure of which is incorporated herein by reference. The system is based on the principal that when electrical currents are passed through a resistive medium, the voltage sensed can be used to determine the position of a medical device within the body. The system includes three pairs of patch electrodes that are placed on opposed surfaces of the body (e.g., chest and back, left and right sides of the thorax, and neck and leg) and form generally orthogonal x, y, and z axes as well as a reference electrode that is typically placed near the stomach and provides a reference value and acts as the origin of the coordinate system for the navigation system. Sinusoidal currents are driven through each pair of patch electrodes and voltage measurements for one or more position sensors (e.g., electrodes) associated with the medical device are obtained. The measured voltages are a function of the distance of the position sensors from the patch electrodes. The measured voltages are compared to the potential at the reference electrode and a position of the position sensors within the coordinate system of the navigation system is determined. In accordance with this exemplary system, system 18 may include patch electrodes 26, a switch 28, a signal generator 30.

Patch electrodes 26 are provided to generate electrical signals used in determining the position of device 12 within a three dimensional coordinate system 32 of system 18. Electrodes 26 may also be used to generate EP data regarding heart 16. Electrodes 26 are placed orthogonally on the surface of body 14 and are used to create axes specific electric fields within body 14. Electrodes $26_{X1}$, $26_{X2}$ may be placed along a first (x) axis. Similarly, electrodes $26_{Y1}$, $26_{Y2}$ may be placed along a second (y) axis and electrodes $26_{Z1}$, $26_{Z2}$ may be placed along a third (z) axis. Each of the electrodes 26 may be coupled to multiplex switch 28. ECU 20 is configured through appropriate software to provide control signals to switch 28 and thereby sequentially couple pairs of electrodes 26 to signal generator 30. Excitation of each pair of electrodes 26 generates an electromagnetic field within body 14 and within an area of interest such as heart 16. Voltage levels at non-excited electrodes 26 may be filtered and converted and provided to ECU 20 for use as reference values.

In an alternative embodiment of the invention, system 18 may comprise a system that employs magnetic fields to detect the position of device 12 within body 14 such as the system offered for sale under the trademark "GMPS" by Mediguide, Ltd. and generally shown and described in U.S. Pat. No. 7,386,339 entitled "Medical Imaging and Navigation System," the entire disclosure of which is incorporated herein by reference. In such a system, a magnetic field generator may be employed having three orthogonally arranged coils, arranged to create a magnetic field within body 14 and to control the strength, orientation and frequency of the field. The magnetic field generator may be located above or below the patient (e.g., under a patient table) or in another appropriate location. Magnetic fields are generated by the coils and current or voltage measurements for one or more position sensors (e.g. a coil) associated with medical device 12 are obtained. The measured currents or voltages are proportional to the distance of the sensors from the coils thereby allowing a position of the sensors within the coordinate system 32 of system 18.

The position and orientation data from position sensors 24 is input to one or more ECU 20 units. Based on the known position and orientation of the medical device 12, ECU 20 provides a means for registering a volumetric data set 34 within coordinate system 32, generating a volumetric rendering 36 of the region of interest from data set 34 and superimposing a representation of device 12 on rendering 36 based on the position signal generated by sensor 24. ECU 18 may also provide operational control over device 12 and display 22. ECU 20 may comprise one or more programmable microprocessors or microcontrollers or may comprise an application specific integrated circuit (ASIC). ECU 20 may include central processing units (CPU) and input/output (I/O) interfaces through which ECU 20 may receive a plurality of input signals including signals generated by device 12 (and particularly position sensors 24 on device 12) and generate a plurality of output signals including those used to control and/or provide data to device 12 and display 22. In accordance with one embodiment of the present invention, ECU 20 is configured with appropriate programming instructions or code (i.e., software) to perform several steps in a method for displaying a position of device 12 disposed within a region of interest in body 14 as described in greater detail hereinbelow.

In a preferred embodiment, device 12 comprises an intracardiac echocardiography catheter 56 or 72 (FIGS. 4 and 5)

including one or more position sensors 24 (electrodes 60, 62, 64, 66 in catheter 56 and electrodes 66, 78, 80 in catheter 72) and an ultrasound array 58. Sensors 24 are adapted to receive or transmit an electromagnetic field, such as the electromagnetic field from system 18. Preferably, system 18 and sensors 24 resolve the position and orientation of device 12 in six degrees of freedom. In particular, the voltage generated by sensors 24 is processed by one or more ECU 20 units to resolve the position and orientation of sensors 24 and, therefore, device 12 (and, in the case of the intracardiac echocardiography catheters 56, 72 the ultrasound array 58).

Referring again to FIGS. 4 and 5, the ultrasound array 58 can be a linear phased array that, coupled with an appropriate conventional ultrasound unit (not shown), generates two-dimensional ultrasound images. These images are affiliated with the position and orientation data and processed by an ECU 20 unit and combined, based on registering multiple two-dimensional images at known positions and orientations (e.g., two-dimensional images captured by ICE catheter 56 or 72), into a three-dimensional volumetric data set 34. Data set 34 may be resolved into voxels as described hereinbelow.

Figure 2:
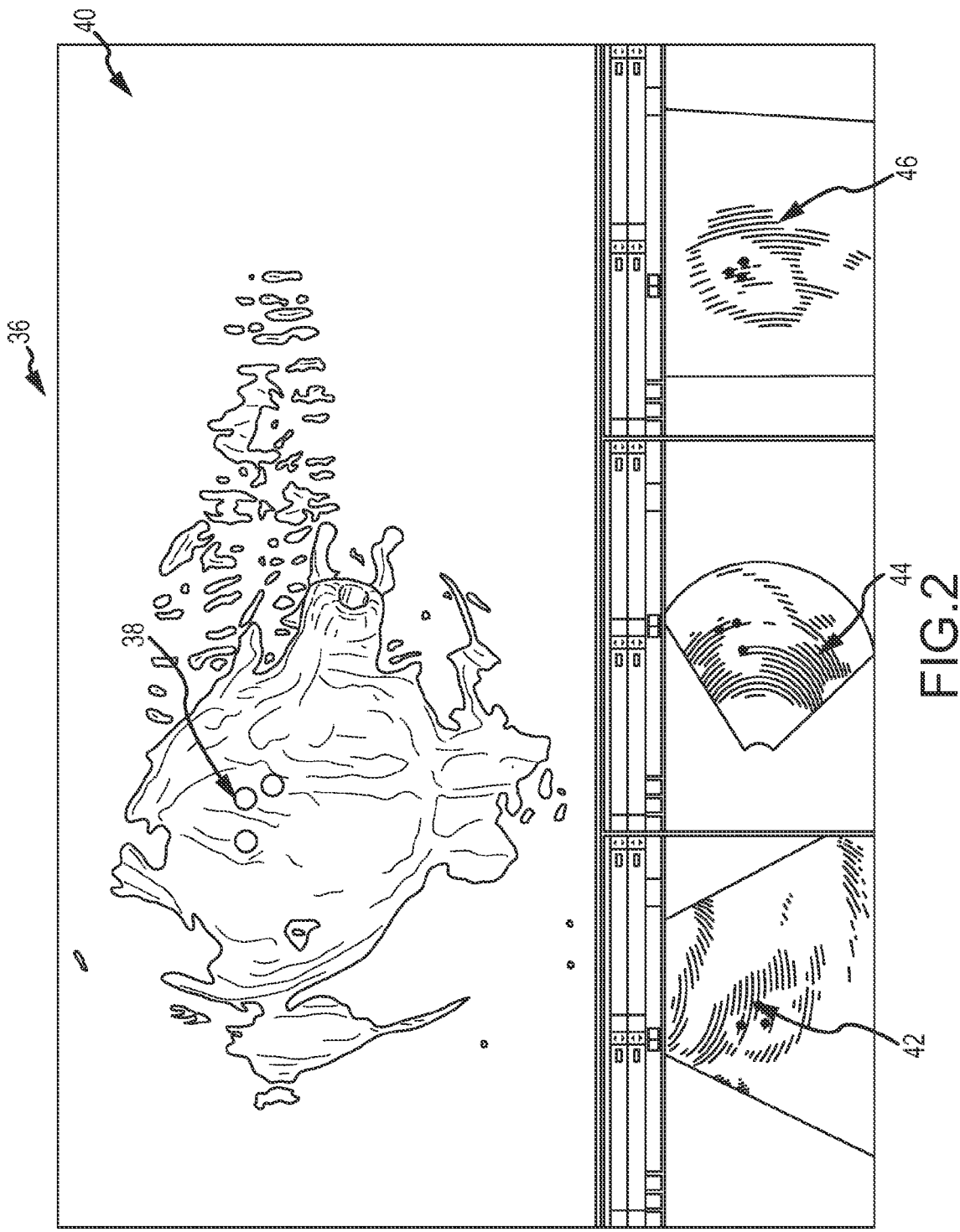
FIG. 2 illustrates a visual display generated by the system of FIG. 1.

Display 22 is provided to convey information to a clinician to assist in diagnosis and treatment. Display 22 may comprise a conventional computer monitor or other display device. Display 22 presents a graphical user interface (GUI) to the physician. The GUI may include a variety of information including, for example, images of a region of interest in body 14, electrophysiological data, graphs illustrating voltage levels over time for various sensors and images of device 12. Referring to FIG. 2, in accordance with the present teachings, display 22 is also configured to display a volumetric rendering 36 of the region of interest and an indication of the position of device 12 within the region of interest. The position of device 12 may be indicated within rendering 36 by superimposing a representation 38 of the position of device 12. In the illustrated embodiment, the position of device 12 is represented by one or more dots. It should be understood, however, that device 12 may be represented in a variety of ways including, for example, by a graphic or icon intended to replicate the size and shape of device 12. Rendering 36 may include a plurality of panels or windows displaying various image of the region of interest including an image 40 comprising a three-dimensional representation (i.e., a ray-casted representation) of the region of interest and images 42, 44, 46 comprising planar cross-sections through the region of interest. In the illustrated embodiment images 42, 44, 46 display planar cross-sections through the region of interest taken along a sagittal plane through body 14, a coronal plane through body 14 and an axial plane through body 14. These images 42, 44, 46 may correspond to the position of device 12 as detected by system 18. In particular, images 42, 44, 46 are preferably registered within coordinate system 32 such that the ECU 20 is able to access and display images 42, 44, 46 from among a plurality of images that may be rendered along sagittal, coronal and transverse planes through body 14 based on the position of device 12. In this manner, display 22 provides the clinician with a three dimensional representation of the position of device 12 along with images of the region of interest taken from various viewpoints.

Figure 3:
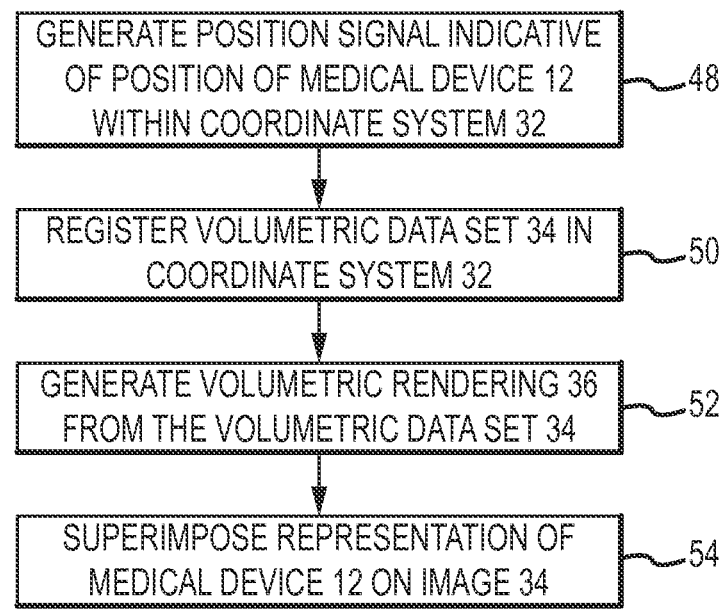
FIG. 3 is a flow chart diagram illustrating a method in accordance with one embodiment of the present teachings.

Referring now to FIG. 3, a method for displaying a position of a medical device, such as device 12, within a region of interest in body 14 will be described. The method may begin with the step 48 of generating a position signal indicative of said position of said medical device within coordinate system 32. Step 44 may include one of the substeps of generating electrical or magnetic fields through body 14. As discussed above, positions sensors 24 disposed on device 12 interact with the electrical and/or magnetic fields generated by system 18 and generate position signals that are provided to ECU 20. ECU 20 determines the position and orientation of sensors 24, and therefore device 12, within coordinate system 32. ECU 20 may also receive position signals from other devices and may determine the position and orientation of such devices within coordinate system 32. These devices may also be shown in display 22 and, in particular, on the volumetric rendering 36.

The method may continue with the step 50 of registering volumetric data set 34 in coordinate system 32. Volumetric data set 34 may consist of a set of intensities, gradients or derived statistical properties for each of several volumetric data elements within the region of interest. In the illustrated embodiment, volumetric data set 34 may be computed by ECU 20 from a series of intracardiac echocardiography images obtained using an ICE catheter 56 or 72. Alternatively, however, volumetric data set 34 may comprise, for example, a magnetic resonance volumetric data set or a computed tomography volumetric data set. The volumetric data set 34 may be stored in a local memory or database (not shown) or in a remote memory or database accessible by ECU 20 over a telecommunications network. ECU 20 includes a registration module for registering volumetric data set 34 within coordinate system 32. The module includes an input interface configured to receive the position and orientation of device 12. Where volumetric data set 34 is computed from a series of intracardiac echocardiography images obtained by an ICE catheter 56 or 72 having a position sensor 24, ECU 20 may associate each image obtained by ICE catheter 12 with a position and orientation within coordinate system 32 based on the location of the ICE catheter within system 32. When volumetric data set 34 is computed from a series of CT or MR images, registration may be accomplished through the use of fiducial markers in the images having a known position in coordinate system 32 or by using a reference sensor at a fixed location relative to the CT or MR systems or in other ways customary in the art.

The method may continue with the step 52 of generating a volumetric rendering 36 from the volumetric data set 34. ECU 20 includes a generation module for generating rendering 36 from data set 34. The generation module may include an input interface configured to receive volumetric data set 34 and transform data set 34 into a set of voxels. ECU 20 may generate rendering 36 by mapping data from the volumetric data set 34 into a three-dimensional voxel model. A volumetric data element contains coordinates for locating the element in space as well as one or more properties such as intensity, intensity gradient or derived statistical properties. A voxel, or volumetric picture element, contains coordinates for locating the element in space as well as one or more display elements. For example, a voxel V may be represented by a coordinate value for each of the x, y, and z axes and at least one display element data value, such as intensity, opacity or a color value. Thus, a voxel could be described by the formula:

$$V=[x,y,z,D_1,D_2,\ldots,D_n]$$

Where x, y, and z represent the axis coordinate values and $D_1, D_2, \ldots, D_n$, represent data values. As image data sets representing slices of different planes through the region of interest are mapped into the voxel model a three dimensional model is created. In the illustrated embodiment, a transfer function is used to compute voxel opacity and color as a function of the corresponding properties of the data elements. ECU 20 then projects the voxel model directly into a two-dimensional image 40 to form a three-dimensional representation of the region of interest by casting a ray of light from each of the pixels in image 40 in a direction normal to the viewing plane. As the ray of light encounters a voxel, the color and opacity values are used to create a shaded voxel sample. For a given ray, these shaded samples are then stacked in visitation order such that the first sample is on top of the stack and the last sample is on the bottom. The stacked samples are then composited according to a rendering equation to calculate the color of the pixel at the origin of the ray. Referring again to FIG. 2, in the illustrated embodiment, rendering 36 may further includes images 42, 44, 46 taken through planar cross-section through volumetric data set 34. In the illustrated embodiment, images 42, 44, 46 are taken through sagittal, coronal and axial planes. Because the volumetric data set 34 used to generate images 42, 44, 46 is registered within coordinate system 32, display 22 may display images 42, 44, 46 reflecting planes encompassing the identified position of device 12 to provide the clinician a multitude of views of the area within the region of interest where device 12 is positioned.

The method may continue with the step 54 of superimposing a representation of medical device 12 on images 40, 42, 44, 46 responsive to position signal generated by sensor 24 on device 12. Because images 40, 42, 44, 46 are registered in the same coordinate system 32 with the position of device 12, ECU 20 is capable of locating device 12 within an appropriate location in images 40, 42, 44, 46 such that images 40, 42, 44, 46 present an accurate visual depiction of the location of device 12 within the region of interest. ECU 20 therefore includes a superimposition module for superimposing a representation of device 12 on rendering 36. As noted above, the position of device 12 may be represented in a variety of ways including, for example, by a graphic or icon intended to replicate the size and shape of device 12.

A system and method in accordance with the present teachings is advantageous as compared to conventional systems and methods because the inventive system and method provide a more accurate and realistic image of the region of interest and of the position of the medical device within the region of interest. As a result, the clinician can more readily navigate medical devices within the region of interest as well as identify structures of interest within the region of interest.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A system for displaying a position of a medical device disposed within a region of interest in a body, said region of interest occupying a three-dimensional space, comprising:

a position sensing system disposed outside of said body and configured to interact with a position sensor on said medical device upon generation of at least one of an electric field and a magnetic field, said position sensor generating a position signal indicative of said position of said medical device within a coordinate system; and an electronic control unit comprising:
a registration module for registering a volumetric data set within said coordinate system, said registered volumetric data set comprising a data set including properties and coordinates within said coordinate system for each of a plurality of volumetric data elements, said volumetric data elements corresponding to an entirety of said three-dimensional space;
a generation module for generating a volumetric rendering of said region of interest from said registered volumetric data set by transforming the volumetric data elements into volumetric picture elements comprising data and by mapping said data from the volumetric picture elements into a three-dimensional voxel model within said coordinate system using said coordinates; and
a superimposition module for superimposing a representation of said medical device within said volumetric rendering using said position signal to depict said representation within said coordinate system;
wherein said medical device comprises an intracardiac electrocardiography catheter; and
wherein said intracardiac electrocardiography catheter generates images comprising said volumetric data set, and said registration module includes an input interface configured to receive position and orientation of the catheter from the position signal to associate said images generated by said catheter with the coordinates.

2. The system of claim 1 wherein said volumetric data set is an intracardiac echocardiography volumetric data set.

3. The system of claim 2 wherein said intracardiac echocardiography catheter includes an array of ultrasound transducers.

4. The system of claim 3 wherein said medical device includes a plurality of position sensors, said plurality of position sensors configured to locate said medical device with six degrees of freedom in said at least one of an electric field and a magnetic field.

5. The system of claim 4 wherein said registration module comprises an input interface, said input interface configured to receive a position and an orientation of said medical device.

6. The system of claim 2 wherein said generation module comprises an input interface, said input interface configured to receive said volumetric data set and said generation module further configured to transform said volumetric data set into a set of voxels.

7. The system of claim 1 wherein said position sensing system includes a plurality of pairs of patch electrodes disposed on opposed external surfaces of said body, an axis between each pair of patch electrodes orthogonal to an axis between other pairs of patch electrodes.

8. The system of claim 1 wherein said position sensing system includes a magnetic field generator.

9. The system of claim 1 further comprising a display for displaying said volumetric rendering.

10. The system of claim 1 wherein said volumetric rendering includes a three-dimensional representation of said region of interest and a planar cross-section through said region of interest.

11. The system of claim 10 wherein said volumetric data set is generated from a plurality of two-dimensional slice images obtained by said catheter.

12. The system of claim 1 wherein said volumetric data set comprises a set of properties for each of a said plurality of volumetric data elements.

13. The system of claim 1 wherein said generation module is configured to:
create a voxel model from said volumetric data set, each voxel in said voxel model having a value for at least one of intensity, color and opacity; and
project the voxel model into a two dimensional image by casting a ray of light from each pixel in the two dimensional image in a direction normal to the viewing plane of the two-dimensional image and through at least one voxel in the voxel model.

14. The system of claim 1 wherein said properties comprise at least one of an intensity and an intensity gradient for each of said plurality of volumetric data elements.

15. The system of claim 1 wherein said data set for each of said plurality of volumetric data elements comprises a data set for each of a plurality of points contained within each volumetric data element.

16. The system of claim 1 wherein said registration module registers one or more points located on an outer surface of a volume defined by said volumetric data set within said coordinate system and one or more points contained within said outer surface of said volume within said coordinate system.

17. The system of claim 1 wherein generating said volumetric rendering further comprises the following:
generating a two-dimensional image from the three-dimensional voxel model by casting a ray of light from each pixel of the three-dimensional voxel model;
creating shaded voxel samples by obtaining color and opacity values as the ray encounters voxels; and
compositing the shaded voxel samples to calculate the color of the pixel at the origin of the ray.

18. The system of claim 1 wherein the superimposition module superimposes said representation of said medical device within said volumetric rendering.

19. The system of claim 1 wherein said superimposed representation of said medical device is responsive to changes in the position signal.

20. A method for displaying a position of a medical device disposed within a region of interest in a body, said region of interest occupying a three-dimensional space, comprising the steps of:
generating a position signal indicative of said position of said medical device within a coordinate system, said position signal generated by a position sensor disposed on said medical device and configured to interact with a position sensing system disposed outside of said body upon generation of at least one of an electric field and a magnetic field;
registering a volumetric data set within said coordinate system, said registered volumetric data set comprising a data set including properties and coordinates within said coordinate system for each of a plurality of volumetric data elements, said volumetric data elements corresponding to an entirety of said three-dimensional space;
generating a volumetric rendering of said region of interest from said registered volumetric data set by transforming the volumetric data elements into volumetric picture elements comprising data and by mapping said data from the volumetric picture elements into a three-dimensional voxel model within said coordinate system using said coordinates; and
superimposing a representation of said medical device within said volumetric rendering using said position signal to depict said representation within said coordinate system;
wherein said medical device comprises an intracardiac electrocardiography catheter; and
wherein said intracardiac electrocardiography catheter generates images comprising said volumetric data set, and wherein registering a volumetric data set within said coordinate system comprises associating said images generated by said catheter with the coordinates.

21. The method of claim 20 wherein said volumetric data set is an intracardiac echocardiography volumetric data set.

22. The method of claim 20 wherein said step of generating a position signal includes the substep of generating electrical fields along a plurality of orthogonal axes through said body.

23. The method of claim 20 wherein said step of generating a position signal includes the substep of generating magnetic fields along a plurality of orthogonal axes through said body.

24. The method of claim 20 further comprising the step of displaying said volumetric rendering.

25. The method of claim 20 wherein said volumetric rendering includes a three-dimensional representation of said region of interest.

26. The method of claim 25 wherein said volumetric rendering further includes a planar cross-section through said region of interest.

27. A system for displaying a position of a medical device disposed within a region of interest in a body, said region of interest occupying a three-dimensional space, comprising:
means for generating a position signal indicative of a position of said medical device within a coordinate system; and
means for registering a volumetric data set within said coordinate system, said registered volumetric data set comprising a data set including properties and coordinates within said coordinate system for each of a plurality of volumetric data elements, said volumetric data elements corresponding to an entirety of said three-dimensional space;
means for generating a volumetric rendering of said region of interest from said registered volumetric data set by transforming the volumetric data elements into volumetric picture elements comprising data and by mapping said data from the volumetric picture elements into a three-dimensional voxel model within said coordinate system using said coordinates; and
means for superimposing a representation of said medical device within said volumetric rendering using said position signal to depict said representation within said coordinate system;
wherein said medical device comprises an intracardiac electrocardiography catheter; and
wherein said intracardiac electrocardiography catheter generates images comprising said volumetric data set, and wherein said means for registering a volumetric data set within said coordinate system comprises means for associating said images generated by said catheter with the coordinates.

* * * * *